United States Patent [19]

Jain

[11] Patent Number: 5,250,072
[45] Date of Patent: Oct. 5, 1993

[54] SURGICAL CLAMP JAW COVER

[76] Inventor: Krishna M. Jain, 8405 Plover, Kalamazoo, Mich. 49002

[21] Appl. No.: 624,981

[22] Filed: Dec. 10, 1990

[51] Int. Cl.$^5$ .............................................. A61B 17/00
[52] U.S. Cl. ................................... 606/205; 606/207
[58] Field of Search .............. 606/205, 206, 207, 208, 606/209, 210, 151; 81/418, 419, 420, 421, 422, 423, 424; D24/143; 74/551.1, 551.9, 558.5, 557, 558

[56] References Cited

U.S. PATENT DOCUMENTS

| D. 295,219 | 4/1988 | Scanlan | D24/143 |
| 1,422,538 | 7/1922 | Cameron | 606/207 |
| 2,121,989 | 6/1938 | Schnase et al. | 74/558.5 |
| 2,704,668 | 3/1955 | Park | 74/551.9 |
| 4,702,702 | 10/1987 | Mikelsaar | 81/418 |

Primary Examiner—C. Fred Rosenbaum
Assistant Examiner—Manuel Mendez
Attorney, Agent, or Firm—Varnum, Riddering, Schmidt & Howlett

[57] ABSTRACT

This relates to a cover for a jaw of a surgical clamp. The cover has an internal surface which is roughened so as to increase the frictional engagement of the interior surface of the cover with a surgical clamp jaw. The roughening of the interior surface of a cover may be accomplished as a true roughened surface or may be in the form of a plurality of axially spaced, annular ridges molded on to the internal surface of a tubular body of the cover.

20 Claims, 1 Drawing Sheet

SURGICAL CLAMP JAW COVER

This invention relates in general to new and useful improvements in surgical equipment, and more particularly to a cover for a surgical clamp jaw which is specifically constructed so as to be retained on the surgical clamp jaw during use.

BACKGROUND OF THE INVENTION

During surgery, and particularly during vascular surgery, the surgeon typically grasps very fine and delicate sutures during the course of the operation. Conventional surgical clamps are used to grasp the sutures, but in order to protect against damage to the sutures, covers are typically used over the jaws of the clamp. These covers are typically flexible rubberlike tips or boots which slip over the ends of the clamp jaws.

Previously available covers are deficient in that when used in contact with the body, due to the heat of the body, the covers tend to expand and occasionally slip off the ends of the clamp jaws. For this reason, clamp jaw covers are typically made radiopaque so that in the event they are lost in the patient, they can be later found by an examination of an x-ray.

SUMMARY OF THE INVENTION

In accordance with the invention, a surgical clamp jaw cover is provided for a medical clamp having a clamp jaw and serrations on the clamp jaw. The cover comprises a tubular body having an inner surface with projections that engage the serrations on the clamp jaw when the cover is placed over the clamp jaw. The engagement of the projections and the serrations restricts the movement of the cover relative to the clamp jaw and retains the cover on the clamp jaw. Preferably, the projections comprise annular ridges, which are arranged in an axially spaced relation and disposed substantially over the full length of the tubular body.

In one aspect of the invention, the clamp jaw cover has an inner surface with projections that engage the serrations of the clamp jaw to increase the grip of the clamp jaw by the cover. Thus, when a clamp having a cover is used in surgery and the normal coefficient of friction between the rubber like material and the clamp jaw is reduced, the cover will stay retained on the clamp jaw.

In another aspect of the invention, the projections have a rounded cross section. Preferably the projections are randomly disposed on the inner surface of the cover to form a coarse textured surface, which can engage the serrations of the clamp jaw.

The body of the surgical clamp jaw cover has either both ends open or one end open and one end closed. The closed end is preferably rounded.

BRIEF DESCRIPTION OF THE DRAWINGS

The invention will now be described with reference to the drawings in which.

DESCRIPTION OF THE INVENTION

Figure 1:
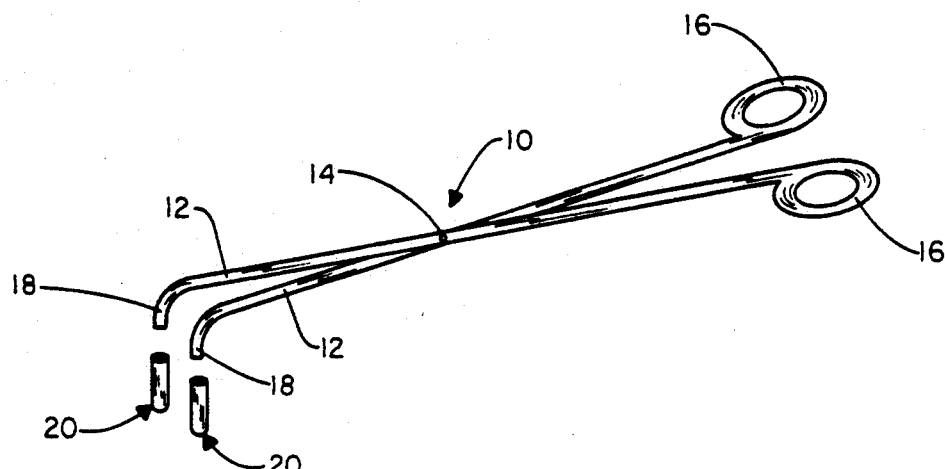
FIG. 1 is a perspective view of a typical surgical clamp having covers on the jaws thereof.

Referring now to the drawings in detail, reference is first made to FIG. 1 wherein there is illustrated a conventional surgical clamp generally identified by the numeral 10. The clamp 10 includes a pair of elongated arms 12 pivotally connected together as at 14 in crossing relation and terminating at first ends in finger receiving handles 16 and at the opposite ends in offset clamping jaws 18. The end portions of the jaws 18 are covered by covers 20 formed in accordance with this invention.

Figure 2:
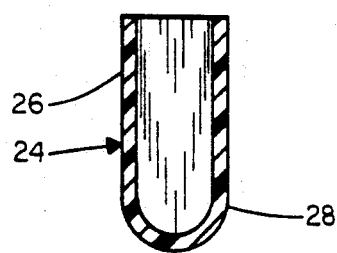
FIG. 2 is an enlarged cross sectional view of a prior art cover.

Reference is next made to the prior art showing of FIG. 2 wherein a cover 24 is illustrated. The cover 24 is formed of a flexible rubberlike material and includes a tubular body 26 and a rounded closed end 28.

Figure 4:
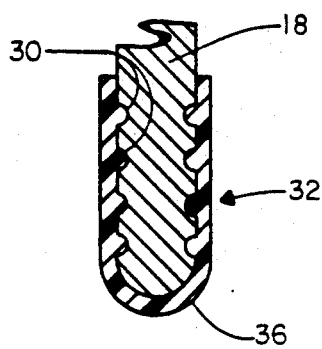
FIG. 4 is an enlarged sectional view of an end portion of a surgical clamp jaw having the cover of FIG. 3 mounted thereon in interlocking relation.

The prior art cover 24 has a smooth interior and since the cover expands due to being heated by the body temperature, has a tendency to slide off of the respective jaws 18 notwithstanding the fact that the surgical clamp jaws 18 are typically provided on end portions thereof with serrations 30 as is best shown in FIG. 4.

Figure 3:
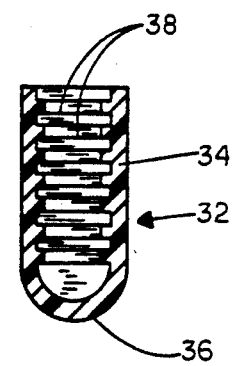
FIG. 3 is an enlarged fragmentary sectional view taken through a cover formed in accordance with this invention.

Referring now to a preferred embodiment of the invention as shown in FIG. 3, there is illustrated a cover generally identified by the numeral 32 which like the cover 24 includes a tubular body 34 open at one end and closed at the opposite end by a rounded closure 36. The cover 32, however, differs from the cover 24 in that it is internally provided with a plurality of axially spaced annular ribs 38 which correspond to the serrations 30 of the surgical clamp jaws 18 as is best shown in FIG. 4. Because of this interlocking gripping relationship, it takes considerable manipulation to remove a cover 32 from a surgical clamp jaw 18.

Figure 5:
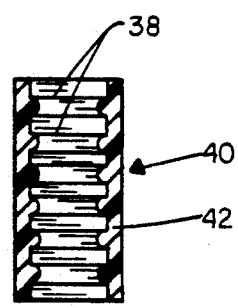
FIG. 5 is an enlarged vertical sectional view taken through a surgical clamp jaw cover open at opposite ends.

Although a typical cover for a surgical clamp jaw has a closed end, such as the closed end 36, it is feasible to provide a cover which is open at both ends, such as the cover 40 shown in FIG. 5. In other words, the cover 40 is formed solely of a tubular body 42 having the internal ribs 38.

Figure 6:
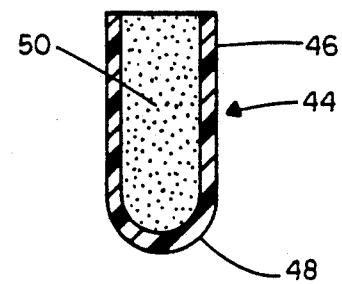
FIG. 6 is an enlarged fragmentary sectional view taken through a cover having a roughened internal surface for frictionally gripping a surgical clamp jaw.

Another form of cover, generally identified by the numeral 44, is shown in FIG. 6. The cover 44 is formed of the same flexible rubberlike material as the cover 32 and includes a tubular body 46 having a closed end 48. However, in lieu of the annular ridges 38 of the cover 32, the interior surface of the body 46 of the cover 44 is merely provided with a roughened surface as at 50. This roughened surface, however, will interlock with the serrations formed on the surgical clamp jaw tip.

The cover with the roughened internal surface 50 may be formed solely of a body open at opposite ends. It is also to be understood that the serrations of the surgical clamp jaw may be other than the groove arrangement 30 shown in FIG. 4.

Returning once again to the cover 44 having a roughened internal surface 50, it is to be understood that the cover 44 may be formed by providing a roughened mold member which functions as a core for the cover 44 and which is dipped into a plastisol compound. The roughened surface 50 may also be formed by abrading the interior surface of the body 46 after the cover 44 has been formed.

Although only several preferred embodiments of the cover have been specifically illustrated and described herein, it is to be understood that minor variations may be made in the cover for a surgical clamp jaw without departing from the spirit and scope of the invention as defined by the appended claims.

The embodiments of the invention in which an exclusive property or privilege is claimed are defined as follows:

1. A surgical clamp jaw cover for a medical clamp having a clamp jaw and serrations on the clamp jaw, said cover comprising a tubular body and said tubular body having an inner surface, said inner surface having projections thereon, whereby when the cover is received on the clamp jaw, the projections will engage the serrations to restrict movement of the cover relative to the clamp jaw for retaining said cover on the clamp jaw.

2. A surgical clamp jaw cover according to claim 1 wherein said projections are in the form of annular ridges.

3. A surgical clamp jaw cover according to claim 2 wherein said annular ridges are disposed substantially the full length of said body.

4. A surgical clamp jaw cover according to claim 2 wherein said annular are arranged in axially spaced relation.

5. A surgical clamp jaw cover according to claim 3 wherein said annular ridges are disposed substantially the full length of said body.

6. A surgical clamp jaw cover according to claim 4 wherein said body has opposite open ends.

7. A surgical clamp jaw cover according to claim 6 wherein one end of said body is open, and an opposite end of said body is closed by a rounded end.

8. A surgical clamp jaw cover according to claim 4 wherein one end of said body is open, and an opposite end of said body is closed.

9. A surgical clamp jaw cover according to claim 1 wherein said projections are rounded in cross section.

10. A surgical clamp jaw cover according to claim 1 wherein said projections are disposed randomly on the inner surface, thereby forming a coarse-textured surface.

11. A surgical clamp jaw cover according to claim 1 wherein said body has opposite open ends.

12. A surgical clamp jaw cover according to claim 1 wherein one end of said body is open, and an opposite end of said body is closed.

13. A surgical clamp jaw cover according to claim 1 wherein one end of said body is open, and an opposite end of said body is closed by a rounded end.

14. A surgical clamp jaw cover for a medical clamp having a clamp jaw and serrations on the clamp jaw, said cover comprising a tubular body formed of a flexible rubberlike material, said tubular body having an inner surface, said inner surface having projections thereon for providing increased gripping of the clamp jaw by the cover whereby when a clamp having said cover is used in surgery and the normal coefficient of friction between said rubberlike material and said clamp jaw is reduced, the cover will stay retained on the clamp jaw.

15. A surgical clamp jaw cover according to claim 13 wherein said projections are disposed randomly on the inner surface, thereby forming a coarse-textured surface.

16. A surgical clamp jaw cover according to claim 14 wherein said projections are in the form of annular ridges.

17. A surgical clamp jaw cover according to claim 16 wherein said internal gripping means is in the form of annular ridges arranged in axially spaced relation.

18. A surgical clamp jaw cover according to claim 14 wherein said body has opposite open ends.

19. A surgical clamp jaw cover according to claim 14 wherein one end of said body is open, and an opposite end of said body is closed.

20. A surgical clamp jaw cover according to claim 14 wherein one end of said body is open, and an opposite end of said body is closed by a rounded end.

* * * * *

UNITED STATES PATENT AND TRADEMARK OFFICE
CERTIFICATE OF CORRECTION

PATENT NO. : 5,250,072

DATED : October 5, 1993

INVENTOR(S) : KRISHNA M. JAIN

It is certified that error appears in the above-identified patent and that said Letters Patent is hereby corrected as shown below:

Column 3, claim 4, line 31, after "annular" insert --ridges--

Signed and Sealed this

Twenty-fourth Day of May, 1994

Attest:

BRUCE LEHMAN

*Attesting Officer*  *Commissioner of Patents and Trademarks*